| United States Patent [19] | [11] | 4,115,576 |
|---|---|---|
| Penn | [45] | Sep. 19, 1978 |

[54] COMPOSITIONS AND METHOD OF EMPLOYING THE SAME FOR INHIBITING ALCOHOL INTOXICATION

[76] Inventor: Nathar W. Penn, 453 Glendale Ave., Wyckoff, N.J. 07481

[21] Appl. No.: 735,145

[22] Filed: Oct. 26, 1976

Related U.S. Application Data

[63] Continuation of Ser. No. 457,226, Apr. 2, 1974, abandoned.

[51] Int. Cl.$^2$ .................. A61K 31/44; A61K 31/455; A61K 31/505
[52] U.S. Cl. ..................................... 424/251; 424/263; 424/266
[58] Field of Search ...................... 424/251, 263, 266

[56] References Cited

U.S. PATENT DOCUMENTS

| 2,433,688 | 12/1947 | Fox et al. ............................ 424/263 |
| 2,628,184 | 2/1953 | Widmann ............................ 424/263 |
| 2,998,350 | 8/1961 | Grunigen et al. ..................... 424/361 |

OTHER PUBLICATIONS

Lunde, Chemical Abstracts, vol. 59, p. 4315, (1963).
Pawan, Chemical Abstracts, vol. 68, p. 7412, (1968).
Pawan, Chemical Abstracts, vol. 69, p. 890, (1968).
Konttinen et al., Chemical Abstracts, vol. 67, p. 3958, (1967).

*Primary Examiner*—Stanley J. Friedman
*Attorney, Agent, or Firm*—Cooper, Dunham, Clark, Griffin & Moran

[57] ABSTRACT

An admixture consisting essentially of two or more of the compounds selected from the group consisting of 5-hydroxymethylcytosine (5-HMC), a $B_6$ vitamin and nicotinamide or nicotinic acid has been found to be effective as an alcohol detoxicant and useful to inhibit alcohol intoxication. There may be added to the aforesaid admixture a calcium ion donor, such as water-soluble calcium salt selected from the group consisting of calcium chloride, calcium nitrate, calcium acetate, calcium sulfate and calcium pantothenate. Also, there may be added to the aforesaid admixture a carbohydrate, such as mannose or fructose and the compound allantoin.

13 Claims, No Drawings

COMPOSITIONS AND METHOD OF EMPLOYING THE SAME FOR INHIBITING ALCOHOL INTOXICATION

This is a continuation, of application Ser. No. 457,226 filed Apr. 2, 1974, now abandoned.

This invention relates to materials useful as alcohol detoxicants or antagonists. In accordance with one embodiment this invention is directed to a composition useful as an alcohol antagonist. In accordance with another embodiment this invention is directed to a method of treating alcohol intoxication.

This invention is related to my copending application, Ser. No. 447,659, filed Mar. 4, 1974, U.S. Pat. No. 4,048,316 entitled "Composition for Mitigating the Physiological Effects of Barbiturate Addiction and Withdrawal Effects, and for Treatment of Barbiturate Poisoning".

The problem of overcoming alcohol intoxication has been a longstanding problem. Various approaches have been suggested to overcome alcohol intoxication. For example, it has been proposed in the case of humans to administer oxygen at a concentration greater than that of air, such as 50–90% $O_2$, for a short period of time. It has also been proposed in the case of alcohol intoxication of humans that strong coffee be liberally administered. It has also been proposed that fructose is useful as an alcohol detoxicant. For the most part, however, these compositions, materials and techniques have not been completely satisfactory.

It is an object of this invention to provide a composition useful as an alcohol antagonist or detoxicant.

It is another object of this invention to provide a procedure for effecting alcohol detoxification.

How these and other objects of this invention are achieved will become apparent in the light of the accompanying disclosure. In at least one embodiment of the practice of this invention at least one of the foregoing objects will be achieved.

It has been discovered that an admixture or composition consisting essentially of two or more of the compounds selected from the group consisting of 5-hydroxymethylcytosine (5-HMC), a vitamin $B_6$ selected from the group consisting of pyridoxal, pyridoxamine and derivatives and mixtures thereof and nicotinamide or nicotinic acid is effective as an alcohol detoxicant and useful to inhibit alcohol intoxication.

The $B_6$ vitamin compounds useful in the preparation of compositions or admixtures in accordance with this invention include pyridoxal, such as pyridoxal hydrochloride and pyridoxal 5-phosphate, and pyridoxamine, such as pyridoxamine dihydrochloride. Mixtures of these vitamin $B_6$ compounds in compositions and admixtures in accordance with this invention are useful.

In compositions of this invention nicotinamide is the preferred component in place of an equimolar amount of nicotinic acid since nicotinic acid tends to cause vasodilation whereas nicotinamide has no side effects. There is also usefully added a calcium ion donor, such as water-soluble calcium salt, e.g. a water-soluble calcium salt selected from the group consisting of calcium chloride, calcium nitrate, calcium acetate, calcium sulfate and calcium pantothenate. Also usefully included in compositions and admixtures in accordance with this invention is a readily water-soluble carbohydrate or sugar, such as mannose and fructose. Allantoin may also be included in compositions and admixtures in accordance with this invention.

One or more of the aforesaid usefully added materials or adjuvants for the effective compounds or admixtures in accordance with this invention consisting essentially of two or more of the compounds 5-HMC, a $B_6$ vitamin identified hereinabove and nicotinamide may be present with the effective compounds or admixtures or administered separately or each of the aforementioned compounds and materials or any combination thereof may be administered separately.

As indicated hereinabove, different combinations of the effective compounds, the combinations of the effective compounds having been found to be useful as alcohol detoxicants, may be usefully employed. Examples of effective compositions are compositions containing the compounds 5-HMC and pyridoxal hydrochloride, compositions containing the compounds nicotinamide and pyridoxal hydrochloride and compositions containing the compounds 5-HMC, nicotinamide and pyridoxal hydrochloride. The activity of these compositions measured statistically by the $t$ test are $p < 0.02$, $p < 0.01$ and $p < 0.01$, respectively. The aforementioned test results indicate that the most effective combination is that of the compounds 5-HMC, nicotinamide and pyridoxal hydrochloride. Also useful is the combination made up of the compounds nicotinamide and pyridoxal hydrochloride.

In the make-up of compositions useful as alcohol detoxicants in accordance with this invention the compounds 5-HMC: a vitamin $B_6$ compound identified hereinabove: nicotinamide or nicotinic acid are usefully present in the molar ratios 1–6: 1–10 and 0.1–10, respectively. The compounds and compositions in accordance with this invention may be administered orally or, as indicated hereinabove, intraveneously or intraperitoneally. When formulated for oral administration, compounds and compositions in accordance with this invention could be formulated in the spansule-form so as to maintain their effectiveness over a period of time. Such formulations would be useful for one who anticipates the intake of a substantial amount of alcohol over a relatively short period of time.

Various tests have been performed to demonstrate the effectiveness of compounds and compositions in accordance with this invention as alcohol detoxicants. The tests or assays were carried out as follows:

Male albino mice in the weight range 20–25 grams were injected intraperitoneally with a 33% aqueous solution by volume of ethyl alcohol. The dosage was adjusted to the lever of 0.4 ml per 20 gram body weight. After injection and when the mice were asleep they were placed on their backs and the time noted. Thereupon the mice were injected intraperitoneally with aqueous solutions of the detoxicant compounds or compositions in accordance with this invention. The volume of the aqueous solution injected was in the amount of 0.6 ml per 20 gram body weight. Controls consisting of water only were also injected. Recovery in the mice was determined by the return of the righting reflexing and the time at which the mouse rolled over was noted. The data obtained in these tests are presented in accompanying Table I. The quantities of the compounds making up the compositions in accordance with this invention and administered to the mice were per 20 gram body weight: 2.76 mg 5-HMC; 0.24 mg nicotinamide and 1.02 mg pyridoxal hydrochloride.

TABLE 1

| SYSTEM | NUMBER OF MICE | SLEEPING TIME IN MINUTES | t TEST COMPARED WITH CONTROL |
|---|---|---|---|
| 1. Control | 20 | 402 | — |
| 2. 5-HMC, pyridoxal hydrochloride | 17 | 248 | p<.02 |
| 3. Pyridoxal hydrochloride nicotinamide | 18 | 235 | p<.01 |
| 4. 5-HMC, pyridoxal hydrochloride and nicotinamide | 18 | 173 | p<.01 |
| 5. At the level of ½* of system 4 | 10 | 240 | p<.05 |

*This lower dosage of antidote still gives a significant reduction in the sleeping time.

According to the Merck Index 100 mg of nicotinamide can be given orally to humans as an upper dosage. On this basis about 1.5 grams of 5-HMC would be employed. These levels would be acceptable for the use of the compositions in accordance with this invention as alcohol detoxicants in the absence of supervised administration.

As indicated hereinabove, the compositions of this invention containing the effective compounds, viz. two or more of the compounds 5-HMC, a selected vitamin $B_6$ compound and nicotinamide or nicotinic acid are useful not only as alcohol detoxicants but also as compositions useful to prevent alcohol intoxication. Usefully, a calcium ion donor is incorporated in the compositions in accordance with this invention.

Additional tests were carried out demonstrating the effectiveness of compositions in accordance with this invention as alcohol detoxicants. The tests were carried out in mice and in rats and were assayed by demonstrated reductions in sleeping time. Each assay was carried out, as described hereinabove, with a minimum of 20 animals, 10 treated and 10 controls. These tests demonstrated that the combination of 5-HMC, nicotinamide and pyridoxal phosphate or pyridoxamine shortened sleeping time as well as the combination of 5-HMC, nicotinamide and pyridoxal hydrochloride. The employment of pyridoxamine as the vitamin $B_6$ compound gave variable results. It may be that the metabolically active form of the $B_6$ vitamin family, usually considered to by pyridoxal phosphate, cannot be readily synthesized from pyridoxine by an intoxicated animal. Accordingly, individual differences would then determine the rate at which the metabolically active form of $B_6$, i.e. pyridoxal phosphate, is formed from its precursor. Calcium, such as calcium derived from calcium chloride, gave significant improvement with pyridoxal. With respect to the water-soluble calcium salt employed no difference was observable between calcium chloride and calcium nitrate. The combination of 5-HMC and pyridoxal as measured by the reduction in sleeping time was less effective than the combination 5-HMC and nicotinamide.

The combination of the three compounds 5-HMC, pyridoxal hydrochloride and nicotinamide administered at the levels mentioned hereinabove was effective for detoxification of alcohol (ethanol) intoxication for the rat. The assay in the rat was carried out in the same manner mentioned hereinabove, i.e. by determining the sleeping time as indicated by the return of the righting reflex. Male rats weighing about 250 grams were used and a 33% solution of alcohol was injected intraperitoneally in the amount to give 3.4 ml per 250 gram body weight. The effectiveness of calcium was not tested in the rat. Additionally, 17 mg of 5-HMC, 4 mg nicotinamide and 17 mg pyridoxal hydrochloride were administered per 250 gram body weight. The results of these tests are set forth in accompanying Table II for mice and accompanying Table III for rats.

TABLE II

| MICE | Sleeping Time (min) | | |
|---|---|---|---|
|  | Control | Test | p |
| 5-HMC, nicotinamide, pyridoxal phosphate | 361 | 171 | <.01 |
| 5-HMC, nicotinamide, pyridoxamine | 338 | 158 | <.01 |
| 5-HMC, nicotinamide, pyridoxine | 397 | 359 | NS* |
| 5-HMC, pyridoxal phosphate | 429 | 335 | <.05 |
| 5-HMC, pyridoxamine | 401 | 227 | <.05 |
| 5-HMC, pyridoxine | 346 | 359 | NS* |
| Nicotinamide, pyridoxal phosphate | 362 | 188 | <.02 |
| Nicotinamide, pyridoxamine | 384 | 212 | <.05 |
| Nicotinamide, pyridoxine | 382 | 334 | NS* |
| 5-HMC, nicotinamide | 411 | 230 | <.05 |
| Pyridoxal, $CaCl_2$ | 419 | 237 | <.02 |
| Pyridoxal, $Ca(NO_3)_2$ | 394 | 201 | <.02 |
| Nicotinamide, $CaCl_2$ | 380 | 228 | <.05 |
| 5-HMC, $CaCl_2$ | 432 | 466 | NS* |

*NS: not significant

TABLE II

| RATS | | Sleeping Time (min) | |
|---|---|---|---|
|  | Control | Test | p |
| (1) 5-HMC, nicotinamide, pyridoxal hydrochloride | 184 | 114 | <.01 |
| (2) 5-HMC, nicotinamide | 162 | 147 | NS* |
| (3) 5-HMC, pyridoxal hydrochloride | 191 | 153 | NS* |
| (4) Nicotinamide, pyridoxal hydrochloride | 221 | 201 | NS* |
| Mortality of Group (1) | 5 of 10 | 2 of 10 | |

*NS: not significant

It was observed that there was no significant difference in the data whether the alcohol detoxicants in accordance with this invention were injected while the animals were in an alcohol-induced sleep or before, e.g. 15 minutes before, the alcohol was administered to the animals. These observations therefore indicate that the detoxicant compositions in accordance with this invention are useful as compositions useful to prevent alcohol intoxication.

Additional tests were carried out with compositions in accordance with this invention consisting essentially of 5-HMC, pyridoxal and nicotinic acid. In these tests 10 treated mice and 10 controls were tested with an average sleeping time of about 200 and about 390 minutes, respectively. The $t$ test of significance gave $p < 0.01$. It has been observed, moreover, that if 5-HMC is administered at twice the level indicated hereinabove, i.e. at a level of about 5.5 mg/20 gm mouse body weight, 5-HMC alone will reduce alcohol-induced sleeping time to just about the borderline of significance. 10 treated mice and 10 controls showed sleeping times of 136 and 228 minutes, respectively. The $t$ test of these data indicates a $p$ value barely under 0.05. At 2.76 mg of 5-HMC per 20 gm mouse body weight $p$ is $< 0.1$ or not significant. These data indicate the 5-HMC might be effective alone as an alcohol detoxicant.

The usefully added adjuvant materials, such as the water-soluble calcium ion donor, e.g. a water-soluble calcium salt such as calcium chloride, calcium nitrate, the water-soluble carbohydrate or sugar, such as mannose and/or fructose, and allantoin, may be employed in any suitable amount in connection with the active compounds and compositions in accordance with this invention. Fructose can be added in very substantial amounts since it is relatively quickly metabolized. Likewise, the calcium ion donor can be added in substantial amounts, less than, the same as or greater than, e.g. 10–20% greater, the total dosage of the active compounds, i.e. the total dosage of 5-HMC, the $B_6$ vitamin compound and nicotinamide and/or nicotinic acid. The calcium ion donor may also be added in an amount equal to one of these compounds. Likewise, the amount of allantoin added may be less than, the same as or greater than the total amount of the active compounds or one of the active compounds.

With respect to the amounts of the active compounds which may be administered, the ranges in amounts per milligram per kilogram of body weight for the detoxification of humans: 10–30 for 5-HMC; 10–30 for the vitamin $B_6$ compound and 7–30 for nicotinamide and/or nicotinic acid, would be useful.

Studies of metabolism in animals are valuable guides to the biochemistry of man, but there are differences which modify the extension of results from one species to another. Qualitative differences include specific reactions or cellular components characteristic of a particular species, and not present in others. Quantitative differences refer to overall metabolic rates, the amounts of certain biochemicals present in the organism and variations in rates of those reactions common to different organisms. The effects of a novel compound are thus not predictable from species to species unless research establishes the site of action, showing it to be a molecule or reaction present in the animal studied. The actions of well known compounds, particularly when these are cellular components whose metabolism has been established to be similar in a wide variety of species, are therefore primarily subject to the quantitative differences among them. This is the case for the materials and compositions of this invention.

The available information regarding biochemical differences indicates that a major variant is metabolic rate, which is extremely high in the mouse as compared with the rat. It is therefore not unexpected that the three component antagonist which is only slightly more effective in the mouse, compared with the other two compound mixtures, is an absolute requirement for activity in the rat. The ability of the mouse to oxidize, detoxify or excrete alcohol is much greater because of its greater metabolic rate. In accordance with this interpretation of the data, it should be noted that a much higher level of alcohol per kilogram is required to produce sleep in the mouse compared with the rat: 20 cc of a 33% ethanol solution, versus 13.6 cc, respectively. The greater activity of the mouse enzymes and the more rapid removal of alcohol in this species are reflected in the smaller number of compounds needed to counteract the intoxication. The lower metabolic rate of the rat corresponds to the requirement for stimulating additional inhibited enzyme reactions in order to restore normal function.

For this reason a number of compounds have been given which exercise small or moderate effects in countering intoxication in the mouse. In a species with a great disparity in metabolic rate compared with the mouse, these limited effects may be transformed into major increases in antagonist action. Thus, in the human, the small but consistent effects of calcium, mannose or allantoin may prove to be significant potentiation of the antagonist action of the basic three component mixture.

The aforementioned disclosure and test data indicate the effectiveness of compositions in accordance with this invention as alcohol detoxicants. The test data also indicate the effectiveness of such compositions as alcohol detoxicants in humans. Since the compounds employed in the detoxicant compositions in accordance with this invention have been previously administered to humans, particularly the $B_6$ vitamin compounds, and nicotinamide and nicotinic acid, it would appear that the data indicated hereinabove of utility is application to the alcohol detoxification of humans.

As will be apparent to those skilled in the art in the light of the foregoing disclosure, many modifications, alterations and substitutions are possible in the practice of this invention without departing from the spirit or scope thereof.

I claim:

1. A composition useful for combatting alcohol intoxication consisting essentially of 5-hydroxymethylcytosine, a $B_6$ vitamin selected from the group consisting of pyridoxal and derivatives or mixtures thereof, and nicotinamide or nicotinic acid, or mixtures thereof, said 5-hydroxymethylcytosine, said $B_6$ vitamin, and said nicotinamide or nicotinic acid being present in said composition in the molar ratio 1–6: 1–10: 1–10, respectively.

2. A method of combatting alcohol intoxication in a subject which comprises administering to the subject a composition in accordance with claim 1, the components of said composition being administered to said subject in an amount in milligrams per kilogram of subject body weight in the range 10–30 5-hydroxymethylcytosine, 10–30 said $B_6$ vitamin, and 7–30 nicotinamide or nicotinic acid.

3. A composition useful for combatting alcohol intoxication consisting essentially of 5-hydroxymethylcytosine and a $B_6$ vitamin selected from the group consisting of pyridoxal and pyridoxamine, said 5-hydroxymethylcytosine and said $B_6$ vitamin being present in said composition in the molar ratio 1–6:1–10, respectively.

4. A composition in accordance with claim 3 wherein said $B_6$ vitamin is pyridoxal hydrochloride.

5. A composition in accordance with claim 3 wherein said $B_6$ vitamin is pyridoxal.

6. A composition in accordance with claim 3 wherein said $B_6$ vitamin is pyridoxamine.

7. A composition in accordance with claim 3 wherein said $B_6$ vitamin is pyridoxamine dihydrochloride.

8. A method of combatting alcohol intoxication in a subject which comprises administering to the subject a composition in accordance with claim 3, the components of said composition being administered to said subject in an amount in milligrams per kilogram of subject body weight in the range 10–30 5-hydroxymethylcytosine and 10–30 said $B_6$ vitamin.

9. A method in accordance with claim 8 wherein said composition is administered orally.

10. A composition in accordance with claim 8 wherein said composition is administered by injection in a physiologically acceptable carrier.

11. A composition in accordance with claim 8 wherein said composition is administered intraperitoneally in a physiologically acceptable carrier.

12. A composition in accordance with claim 8 wherein said composition is administered intravenously in a physiologically acceptable carrier.

13. A method in accordance with claim 8 wherein the subject is a human.

* * * * *

UNITED STATES PATENT AND TRADEMARK OFFICE
CERTIFICATE OF CORRECTION

PATENT NO. : 4,115,576
DATED : September 19, 1978
INVENTOR(S) : Nathar W. Penn

It is certified that error appears in the above-identified patent and that said Letters Patent are hereby corrected as shown below:

Claim 10, line 1, "A composition in accordance with" should read --A method in accordance with--.

Claim 11, line 1, "A composition in accordance with" should read --A method in accordance with--.

Claim 12, line 1, "A composition in accordance with" should read -- A method in accordance with --."

Signed and Sealed this

Thirteenth Day of February 1979

[SEAL]

Attest:

RUTH C. MASON
Attesting Officer

DONALD W. BANNER
Commissioner of Patents and Trademarks